United States Patent
Vandermey

(10) Patent No.: US 7,838,822 B2
(45) Date of Patent: Nov. 23, 2010

(54) LINEAR FAIMS POWER SUPPLY

(75) Inventor: John Vandermey, Georgetown (CA)

(73) Assignee: DH Technologies Development Pte. Ltd., Singapore (SG)

( * ) Notice: Subject to any disclaimer, the term of this patent is extended or adjusted under 35 U.S.C. 154(b) by 267 days.

(21) Appl. No.: 12/260,066

(22) Filed: Oct. 28, 2008

(65) Prior Publication Data

US 2009/0140138 A1 Jun. 4, 2009

Related U.S. Application Data

(60) Provisional application No. 60/986,907, filed on Nov. 9, 2007.

(51) Int. Cl.
*H01J 49/00* (2006.01)
*B01D 59/44* (2006.01)

(52) U.S. Cl. .................. 250/282; 250/281; 250/290; 250/293

(58) Field of Classification Search .......... 250/281, 250/282, 290, 293, 286, 287
See application file for complete search history.

(56) References Cited

U.S. PATENT DOCUMENTS

| | | | |
|---|---|---|---|
| 5,801,379 A | 9/1998 | Kouznetsov | |
| 6,340,814 B1 * | 1/2002 | Vandermey | 250/292 |
| 2003/0146377 A1 * | 8/2003 | Miller et al. | 250/286 |
| 2004/0124350 A1 * | 7/2004 | Miller et al. | 250/286 |
| 2005/0145789 A1 * | 7/2005 | Miller et al. | 250/290 |
| 2005/0269500 A1 | 12/2005 | Potvin et al. | |
| 2006/0038119 A1 | 2/2006 | Guevremont et al. | |
| 2007/0084999 A1 * | 4/2007 | Miller et al. | 250/288 |
| 2009/0057546 A1 * | 3/2009 | Giles | 250/282 |
| 2010/0129785 A1 * | 5/2010 | Pris et al. | 435/5 |

FOREIGN PATENT DOCUMENTS

| EP | 1391912 A2 | 2/2004 |
|---|---|---|
| EP | 1505397 A1 | 2/2005 |

OTHER PUBLICATIONS

Krylov, E.V., Comparison Of The Planar And Coaxial Field Asymmetrical Waveform Ion Mobility Spectrometer (FAIMS), International Journal Of Mass Spectrometry, Feb. 1, 2003, pp. 39-51, vol. 225, No. 1, Elsevier B.V.

"Notification Concerning Transmittal Of International Preliminary Report On Patentability (Chapter I Of The Patent Cooperation Treaty)" For PCT/US2008/012268, May 20, 2010, 7 Pages, The International Bureau Of WIPO, Geneva, Switzerland.

"Notification Of Transmittal Of The International Search Report And The Written Opinion Of The International Searching Authority, Or The Declaration" For PCT/US2008/012268, Sep. 17, 2009, 10 pages, The International Searching Authority, Rijswijk, The Netherlands.

* cited by examiner

*Primary Examiner*—Bernard E Souw
(74) *Attorney, Agent, or Firm*—Kurt Rauschenbach; Rauschenbach Patent Law Group, LLP

(57) ABSTRACT

In various embodiments the present teachings provide high-voltage, asymmetric-waveform power supplies useful for, e.g., differential mobility spectrometry. In various embodiments, provided are high-voltage, asymmetric-waveform power supplies for high-field asymmetric waveform ion mass spectrometers having field values greater than about 5,000 volts $cm^{-1}$ and varying in time at rates greater than about 600 kilohertz (KHz).

22 Claims, 6 Drawing Sheets

LINEAR FAIMS POWER SUPPLY

CROSS-REFERENCE TO RELATED APPLICATIONS

The present application claims priority to U.S. Provisional Patent Application Ser. No. 60/986,907, filed on Nov. 9, 2007. The entire contents of U.S. Provisional Patent Application Ser. No. 60/986,907 are incorporated herein by reference.

INTRODUCTION

Differential mobility spectrometers are a class of ion spectroscopy instruments that can separate ions based upon their differences in the ratio of high field to low field mobility. Such instruments are useful for analyzing composition of materials, and can provide useful information for the fields of life sciences, e.g. proteomics and modeling the biological functions of biomolecules present in living organisms, and forensics and national security, e.g. detecting the presence of chemical constituents or chemical and biological agents.

A high-field asymmetric waveform ion mass spectrometer (FAIMS) is a type of spectrometer that can provide separation of ionic species present in a gas of ions. In various embodiments, a FAIMS includes parallel electrode plates which are excited with high-voltage signals. Ions pass through the gap between the parallel electrodes, in a direction orthogonal to the high electric field created by the high-voltage signals and can be spatially separated based on differences in the ratio of high field to low field mobility.

SUMMARY

The present teachings provide high-voltage, asymmetric-waveform power supplies useful for, e.g., differential ion mass spectrometry. In various embodiments, a high-voltage source of the present teachings creates electric fields between the electrodes greater than about 5,000 volts $cm^{-1}$, and provides an asymmetric waveform operating at a repetition rate of greater than about 600 kilohertz (KHz).

In various embodiments, a high-voltage asymmetric-field-generating apparatus comprises a first electrode and a second electrode. The first and second electrode are oriented either parallel to each other or are concentric cylinders and are separated by a gap. A first high-voltage waveform generator can be connected to the first electrode, and a second high-voltage waveform generator can be connected to the second electrode. Each waveform generator can be capable of producing a sinusoidal waveform. In various embodiments, the first waveform generator produces a sinusoidal output signal at a first frequency and at a first amplitude, and the second waveform generator produces a sinusoidal waveform at a second frequency and at a second amplitude. Each waveform generator can provide manual or electronically-programmable control of the output waveform's amplitude and/or frequency. The asymmetric field-generating apparatus can include a phase adjusting circuit adapted to adjust the phase of at least one of the waveform generators. In operation, the electric field created between the first electrode and second electrode, resulting from the application of the first high-voltage waveform and second high-voltage waveform to their respective electrodes, can be asymmetric and have a time-averaged value substantially equal to zero. In various embodiments, the magnitude of the electric field created between the electrodes is greater than about 5,000 volts $cm^{-1}$ and varies at a repetition rate of greater than about 600 kilohertz.

The high-voltage asymmetric-field-generating apparatus can further include a direct-current (DC) voltage supply electrically connected to at least one of the two electrodes. This DC supply can provide a compensating DC field between the electrodes, and can enable selection of a particular ion species.

In various embodiments, the field-generating apparatus can further include sensing and feedback control circuitry. In various embodiments, the control circuitry can sense the amplitude ratio of the first waveform generator with respect to the second waveform generator, and provide feedback control to maintain the ratio at a substantially constant value. In various embodiments, the control circuitry can sense the relative phase difference between the signal output from the first waveform generator with respect to the second waveform generator, and provide feedback control to maintain the phase relationship at a substantially constant value.

The field-generating apparatus can include electronic circuitry to derive the frequency for one waveform generator from the other waveform generator. For example, in various embodiments a frequency doubling circuit or device can be used to produce the oscillating frequency for the second waveform generator from the first waveform generator. In various embodiments, a frequency dividing circuit can be used to produce the oscillating frequency for the first waveform generator from the second waveform generator. In various embodiments, a low-pass or band-pass electronic filter can be used to select the oscillating frequency for the first waveform generator from the second waveform generator.

In various embodiments, provided are methods for providing an asymmetric electric field for differential mobility spectrometry comprises providing a first electrode substantially parallel to a second electrode and/or parallel cylindrical electrodes, applying to the first electrode a first high-voltage substantially sinusoidal waveform at a first frequency and at a first amplitude, and applying to the second electrode a second high-voltage substantially sinusoidal waveform at a second frequency and at a second amplitude. In various embodiments, the methods can include selecting the second frequency to be substantially a harmonic of the first frequency value. For example, the second frequency can be n times the first frequency where n is an even integer. In various embodiments, the methods comprise selecting the ratio of the first amplitude to the second amplitude and the relative phase difference between the first waveform and second waveform to provide an electric field between the first electrode and second electrode which is asymmetric and has a time-averaged value substantially equal to zero. In various embodiments, the magnitude of the electric field created between the electrodes is selected to be greater than about 5,000 volts $cm^{-1}$ (V/cm) and is varied at a repetition rate of greater than about 600 kilohertz (KHz). In various embodiments, the magnitude of the electric field created between the electrodes is selected to be greater than about one or more of (a) 5,000 V/cm, (b) 7,000 V/cm and/or (c) 10,000 V/cm and has a repetition rate of greater than about one or more of (a) 600 KHz, (b) 2 MHZ, (c) 3 MHz, and/or (d) 5 MHz.

In various embodiments, methods for providing an asymmetric electric field include applying a direct-current (DC) voltage to at least one of the two electrodes to create a compensating DC field between the electrodes, for selection of a particular ionic species based on it's mobility characteristics.

In various embodiments, methods for providing an asymmetric electric field include sensing and feeding back control signals. In various embodiments, control circuitry can be used to sense the amplitude ratio of the first waveform generator with respect to the second waveform generator, and provide feedback control to maintain the ratio at a substantially constant value. In various embodiments control circuitry can be used to sense the relative phase difference between the signal output from the first waveform generator with respect to the second waveform generator, and provide feedback control to maintain the phase relationship at a substantially constant value.

In various embodiments, methods for providing an asymmetric electric field include deriving the frequency for one waveform generator from the other waveform generator. In various embodiments a frequency doubling circuit or device can be used to produce the oscillating frequency for the second waveform generator from the first waveform generator. In various embodiments, a frequency diving circuit can be used to produce the oscillating frequency for the first waveform generator from the second waveform generator. In various embodiments, a low-pass or band-pass electronic filter can be used to select the oscillating frequency for the first waveform generator from the second waveform generator.

The foregoing and other aspects, embodiments, and features of the present teachings can be more fully understood from the following description in conjunction with the accompanying drawings.

BRIEF DESCRIPTION OF THE DRAWINGS

The figures, described herein, are for illustration purposes only. In the drawings, like reference characters generally refer to like features, functionally similar and/or structurally similar elements throughout the various figures. The drawings are not necessarily to scale, emphasis instead being placed upon illustrating the principles of the teachings. The drawings are not intended to limit the scope of the present teachings in any way.

The features and advantages of the present invention will become more apparent from the detailed description set forth below when taken in conjunction with the drawings.

DETAILED DESCRIPTION OF VARIOUS EMBODIMENTS

The teachings presented herein pertain in various aspects to apparatus and methods for providing time-varying, asymmetric, high-value electric fields useful, e.g., for differential mobility spectroscopy. In various embodiments, the high fields are created by applying sinusoidal high-voltage waveforms from two waveform generators to two substantially parallel electrodes. The sinusoidal waveforms can be synchronized, the amplitudes selected, and the relative phase difference between the two waveforms controllably altered to produce a desired asymmetric, time-varying electric field between the electrodes. In various embodiments, peak electric field values greater than 5,000 volts $cm^{-1}$ can be produced at repetition rates greater than about 600 kilohertz (KHz). Ions traveling between the electrodes can be separated according to their differential high and low-field mobility.

Figure 1:
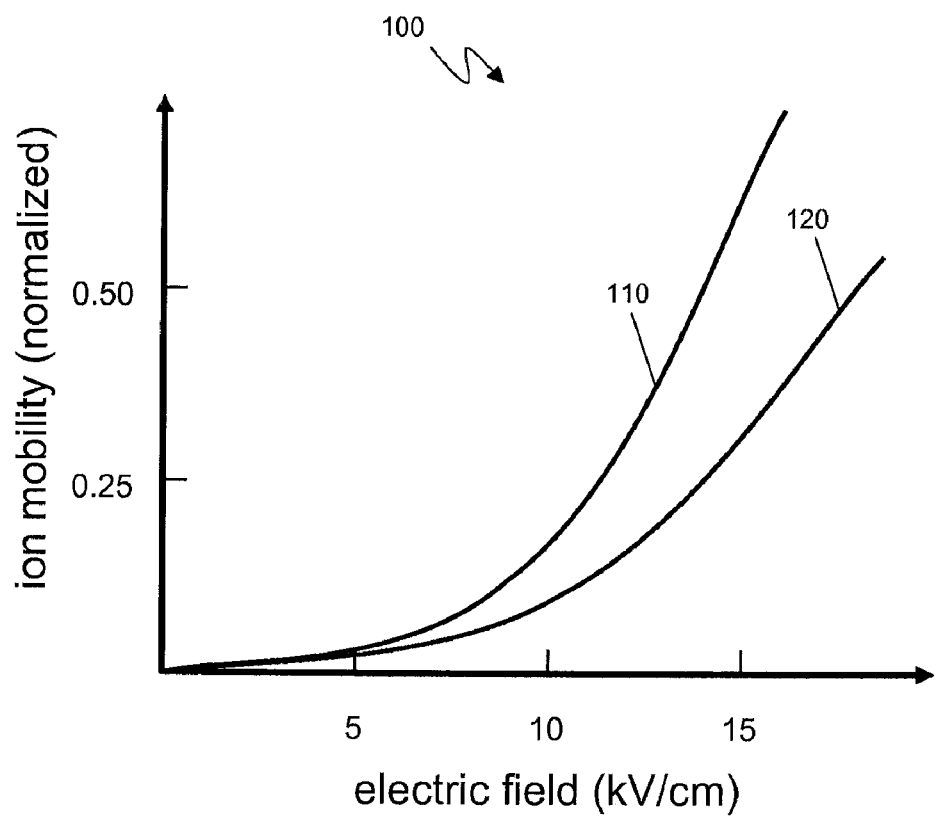
FIG. 1 is a plot of ion mobility as a function of electric field strength for two hypothetical ions.

Different types of ions can exhibit different ion mobilities in the presence of high electric fields and low electrical fields, and these effects can be used to separate ions or select a particular ion. For purposes of understanding, FIG. 1 is an illustrational plot representing two non-linear ion-mobility curves, 110 and 120. Each curve is representative of the behavior of an ion's mobility as a function of electric field for a particular ionic species at a fixed pressure. As is understood in the art, the functional parameter that determines the average ionic energy acquired from the electrical field, sometimes referred to as the "field energy" is the electrical field strength (E) divided by the pressure (p) or gas number density (N), that is, respectively, E/p or E/N. The plotting of ion mobility versus electrical field strength is a well understood convention in the field and used herein for convenience and conciseness of explanation. Accordingly, it is to be understood that increasing the field energy by raising the electrical field strength can also be accomplished by lowering the gas pressure (and hence number density), or a combination of both raising the electrical field strength and lowering the gas pressure. For this reason it is sometimes convenient to discuss field strengths in terms of Townsend units or E/N, whereby at atmospheric pressure the number density for nitrogen molecules is $2.5 \times 10^{19}$ molecules/$cm^3$ at 295° K. Therefore, a 5000 V/cm field would be approximately $2 \times 10^{-16}$ V$cm^2 \times (1 \times 10^{17}$ Td)=20 Td.

Referring again to FIG. 1, in various embodiments, the curves may bend downwards rather than upwards as shown, or they may bend in opposite directions. The nonlinear characteristic of the curves reveals that an ion's mobility is not linearly proportional to the field energy at high field energies. For example, for each of the curves 110 and 120 an ion's mobility within a 10 kV $cm^{-1}$ field is greater than twice the value of the ion's mobility in a 5 kV $cm^{-1}$ field. Were the curves to bend downward, for example, the ion's mobility in a high field would be less than twice its mobility in a field having one-half the high-field value. The nonlinear characteristic combined with differences in the ion mobility curves from ion-to-ion can be used for separation of ions by subjecting the ions to high-value, asymmetric, time-varying electric fields.

Figure 2A:
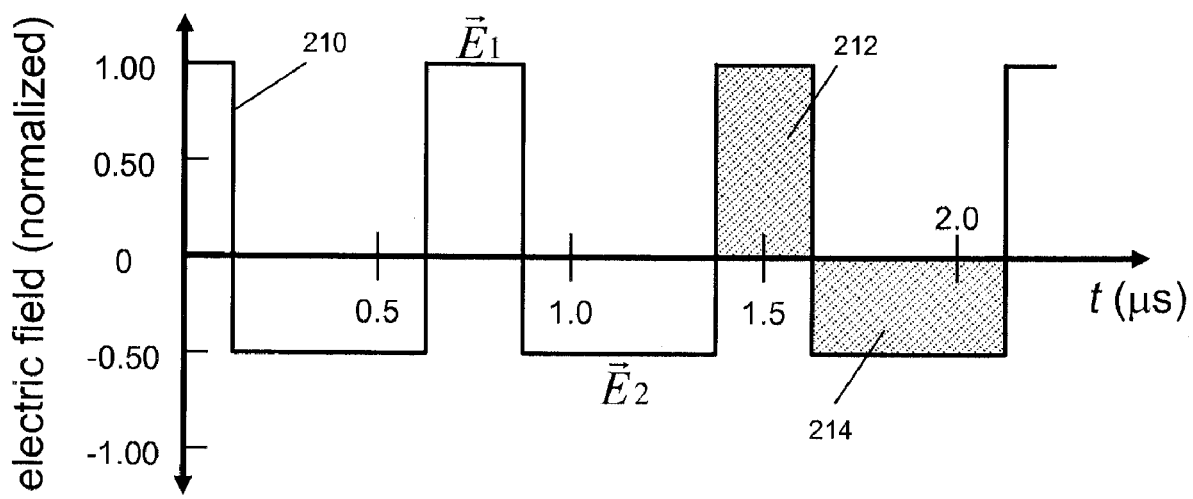
FIGS. 2A-2C represent three embodiments of asymmetric time-varying electric fields. A portion of the waveform 212 has a high field magnitude, $|\vec{E}1|$, and a portion 214 has a low field magnitude, $|\vec{E}2|$.
Figure 2B:
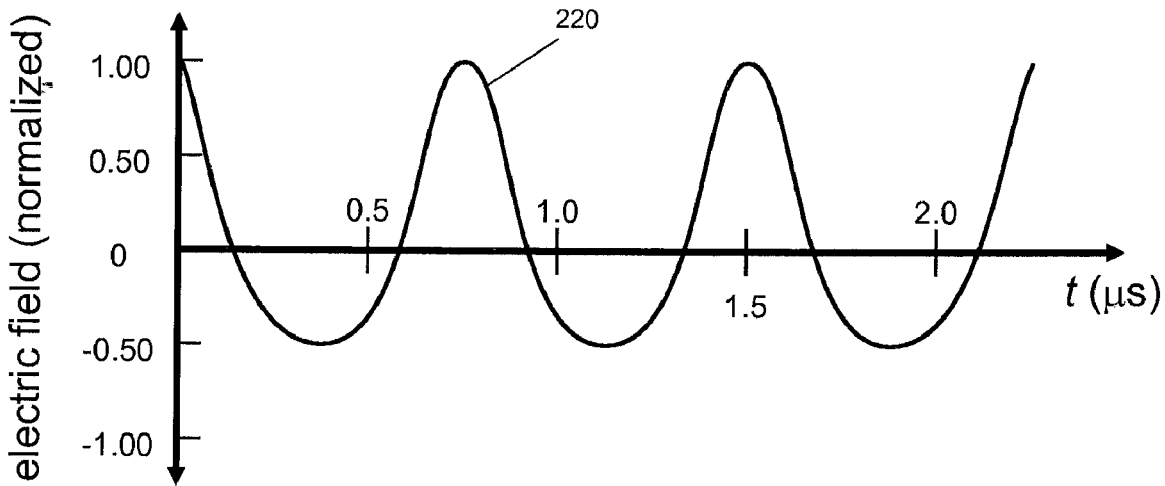
Figure 2C:
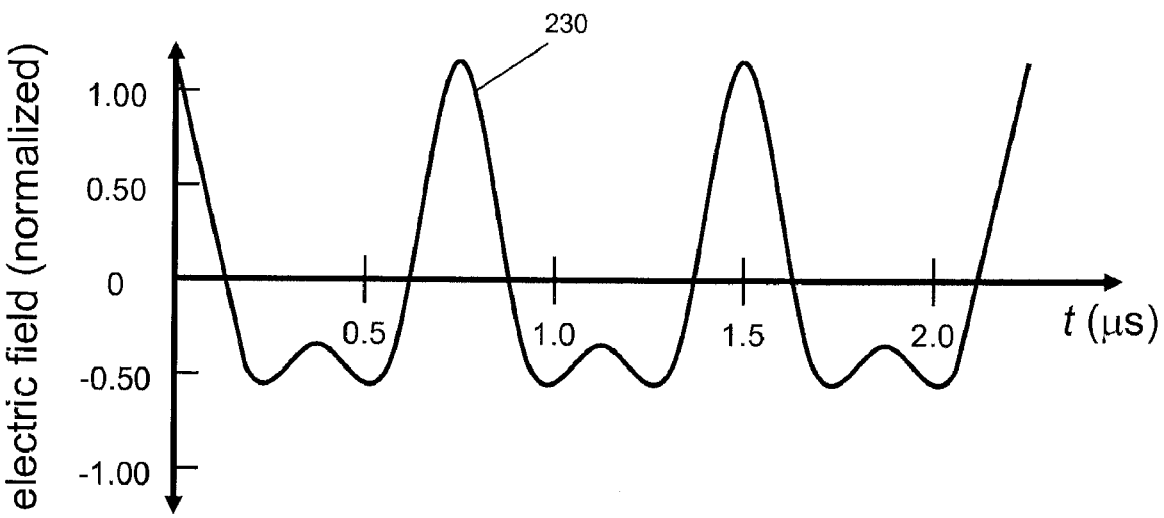
Figure 4A:
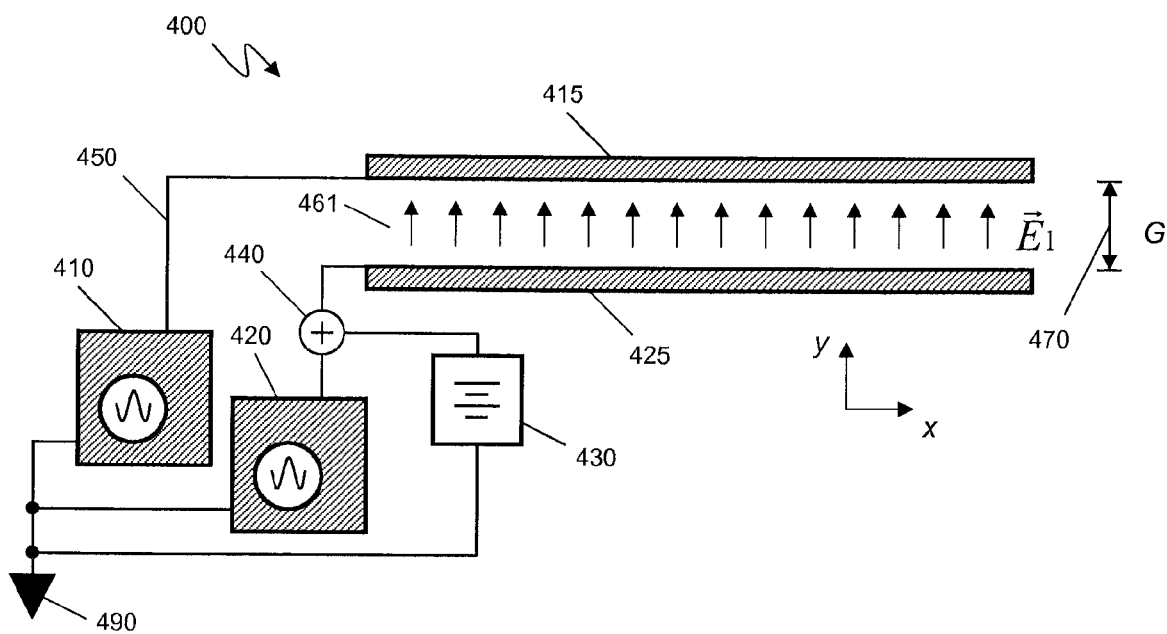
FIGS. 4A-4B are elevational-view illustrations of one embodiment of a high-voltage asymmetric-field-generating apparatus. High-voltage signals from the two waveform generators are applied to each electrode. The resulting electric field between the electrodes varies in time and magnitude in an asymmetric manner.

FIGS. 2A-2C are illustrative plots of asymmetric time-varying electric fields. In various embodiments, these types of fields are used to separate ions in a high-field asymmetric waveform ion mobility spectrometer (FAIMS). Various embodiments of apparatus that can be used in a FAIMS instrument are depicted in FIG. 4A. In various embodiments, electric fields similar to those shown in FIGS. 2A-2C are created between parallel or cylindrical electrodes 415 and 425 in the instrument, and ions travel between the electrodes in the x direction illustrated in the figure. As they travel between the electrodes, the ions experience the time-varying electric fields.

Referring now to FIG. 2A, a square-wave type waveform is shown. In this example, the electric field alternates between a high field value $|\vec{E}1|$ and a low field value $|\vec{E}2|$ with a cycle period of approximately 0.75 microseconds. This period corresponds to a frequency, or repetition rate, of about 1.333 megahertz (MHz). In various embodiments, the repetition rate is one or more of greater than about 600 KHz, greater than about 2 MHz, and/or greater than about 5 MHz. The peak amplitude of the field, shown normalized as 1.00 in the plot, in various embodiments is one or more of greater than about 5,000 V cm$^{-1}$, greater than about 10,000 V cm$^{-1}$, and/or greater than about 15,000 V cm$^{-1}$.

The waveform shown in FIG. 2A has an additional characteristic in that its time-averaged value is zero. This can be represented mathematically as $$\frac{1}{T}\int_0^T E(t)\,dt = 0 \quad (1)$$

where T is the period of the waveform and E(t) is the value of the electric field as a function of time. Graphically, this characteristic means that the shaded region 212 during the positive portion of the waveform has an area equal to that for the region 214 during the negative portion of the waveform. In various embodiments, this characteristic of the waveform can acts to substantially reduce or prevent ions from deviating far from their original trajectory when traveling between electrodes 415 and 425.

An ion with a nonlinear ion-mobility curve as a function of field energy can undergo net motion, or net drift, when subjected to the time-varying field of FIG. 2A, provided the two field values $|\vec{E}1|$ and $|\vec{E}2|$ span a nonlinear portion of the curve. For example, when $|\vec{E}1|$=10 kV/cm and $|\vec{E}2|$=-5 kV/cm, an ion having the mobility curve illustrated in FIG. 1 as 110 will travel further in one direction during the 10 kV/cm portion of the waveform than it will travel in the opposite direction during the -5 kV/cm portion of the waveform. No net motion, or drift, would result for the asymmetric waveform if the ion had a constant mobility at these field energies. In comparison, for example, an ion with a different ion-mobility curve 120 can undergo a different amount of net motion or drift when subjected to the same waveform, and this can be used to separate these two types of ions. It is to be understood that since the separation if based on ion mobility, two ions of the same mass-to-charge ratio but different confirmations (e.g., linear versus branched), for example, can be separated.

FIGS. 2B-2C illustrate non-limiting examples of asymmetric, time-varying electric-field waveforms 220, 230 useful in various embodiments of the present teachings for differential ion mobility spectroscopy. A variety of waveforms are useful in the present teachings including, but not limited to, waveforms having a maximum positive-going value and maximum negative-going value that span a substantially non-linear portion of the ion-mobility curve for the ions under study. In various embodiments, the waveform would also have a time-averaged value approximately equal to zero, although in various embodiments a small positive-value or negative-value offset is added to the waveform.

Referring again to FIG. 4A, different types of ions having different ion-mobility curves as a function of field energy that travel between the electrodes 415 and 425 in the +x direction will undergo different amounts of net drift in the ±y direction when subjected to high-value, time-varying electric fields illustrated in FIGS. 2A-2C. The direction of net drift will depend on the ion charge, the relationship between high and low field mobility, and the orientation of the applied field, e.g. whether $|\vec{E}1|$ points along +y or -y. The application of a small field bias, or offset, can be used to cancel the net drift for a selected species of ions. In various embodiments, the selected species of ions are placed in a "balanced" condition by the application of a small DC bias, and pass through the electrode assembly without colliding with the electrodes. In various embodiments, the DC bias can be applied directly to one electrode. In various embodiments, the DC offset can be added to an asymmetric waveform applied to the electrodes.

Creating a square-wave type waveform, (e.g., such as depicted in FIG. 2A) is often difficult to implement for high-voltage, high-speed applications, because of power and bandwidth demands placed on drive circuitry. Additional complications occur when driving large capacitive loads, such as the electrode assembly of a FAIMS instrument.

Figure 3:
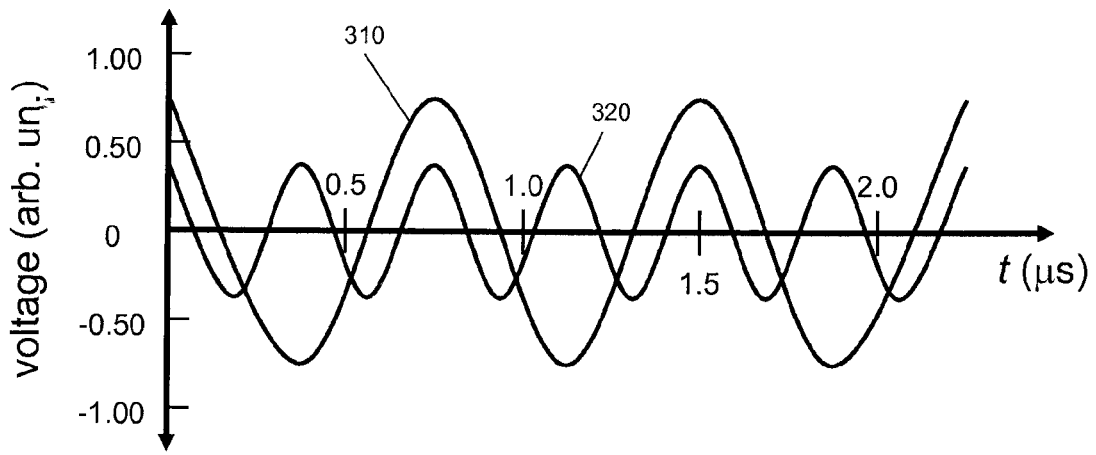
FIG. 3 represents plots of the two high-voltage signals that applied to the electrodes of the apparatus depicted in FIGS. 4A-4B. Adjustment of amplitudes and relative phase are used in this example to create an asymmetric electric field between the electrodes 415, 425 that varies in time as approximately indicated in FIG. 2B or FIG. 2C.

Asymmetric, electric-field waveforms of the type shown in FIGS. 2B-2C can be generated by superposition of two substantially sinusoidal voltage waveforms, e.g. waveforms 310 and 320 as illustrated in FIG. 3, applied to the two electrodes 415 and 425. In various embodiments, one voltage waveform 320 is a harmonic of the other voltage waveform 310. In various embodiments, one waveform is the 2$^{nd}$ harmonic of the other waveform. In various embodiments, more than two waveforms, having harmonic relationships can be applied to the electrodes. By selecting a relative phase difference between the applied voltage waveforms 310 and 320, and by selecting amplitudes for each waveform, asymmetric, electric-field waveforms having desired characteristics can be created between the electrodes.

Mathematically, the electric field between the electrodes can be expressed as $$E(t) = \frac{V_a(t) - V_b(t)}{G} \quad (2)$$

where $V_a(t)$ is the high-voltage waveform 310 applied to one electrode 415, $V_b(t)$ is the high-voltage waveform 320 applied to the other electrode 425, and G is the spacing between the electrodes. The two high-voltage waveforms can be represented as $$Va(t) = Aa\,\cos(2\pi vat + \phi a) \quad (3)$$

$$Vb(t) = Ab\,\cos(2\pi vbt + \phi b) \quad (4)$$

where $A_a$, $A_b$ represent the amplitudes of the waveforms, va, vb represent the frequency of the waveforms, and φa, φb represent the phase of the waveforms. The relative phase difference between the two voltage waveforms can be expressed as φr=φa-φb. In various embodiments, a desired asymmetric electric-field waveform E(t) can be produced by controllably altering a sufficient number of the parameters $A_a$, $A_b$, φa, φb, and G.

In various embodiments, the waveforms $V_a(t)$ and $V_b(t)$ are periodic signals which are not purely sinusoidal or co-sinusoidal, e.g. they may be distorted sine waves, distorted cosine waves, filtered rectified waveforms, or clipped waveforms. In various embodiments, the amplitudes of the voltage waveforms $A_a$, $A_b$ are greater than about 500 volts, greater than about 1,000 volts, and greater than about 2,000 volts. The relative phase difference φr between the voltage waveforms can be any value between about 0 radians and 2π radians. In various embodiments, vb=2va and va is greater than about 600 Khz, greater than about 2 MHz, and greater than about 5 Mhz. The spacing between the electrodes G can be any value between about 0.25 millimeters and about 5 millimeters.

Figure 4B:
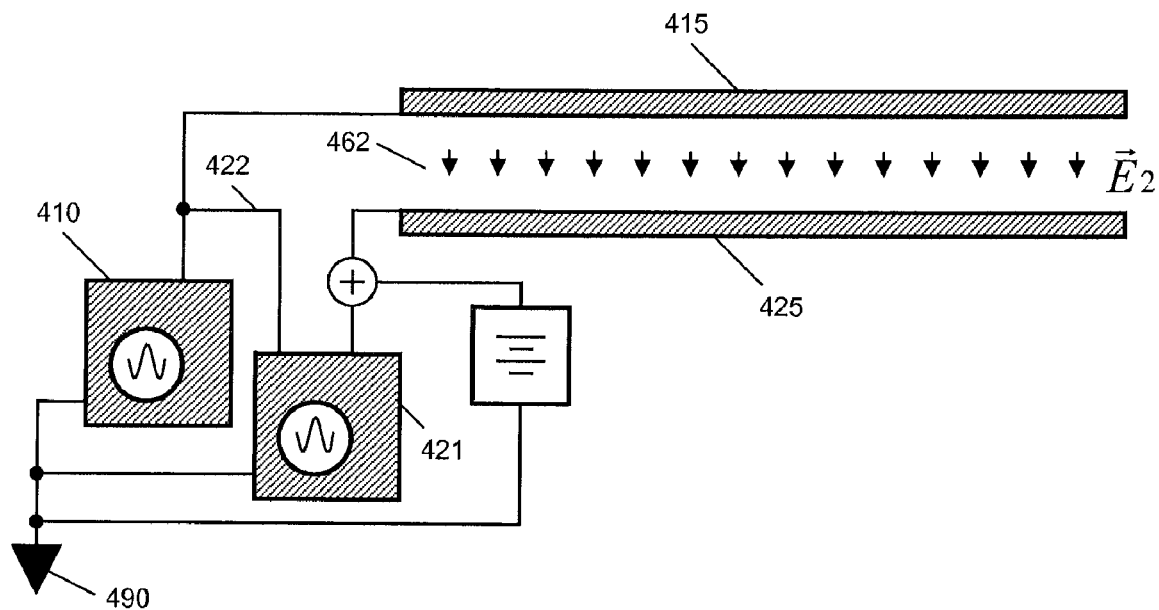

FIGS. 4A-4B depict, in simplified block-diagram form, embodiments of a high-field asymmetric-waveform apparatus 400 for differential mobility spectrometry. In operation, a time-varying, asymmetric, electric field 461, 462 is created between two electrodes 415 and 425. Ions travel between the electrodes, along the x direction, orthogonal to the direction of the time varying field. The high-value, time-varying, asymmetric field imparts a net drift to the ions in the y direction. In various embodiments, one high-voltage waveform generator 410 drives one electrode 415, while a second high-voltage waveform generator 420 drives a second electrode 425. The electrodes can be, e.g., parallel strip electrodes, parallel plate electrodes, concentric cylinders, curved elements, etc. An auxiliary direct-current (DC) power supply 430 can be added to the output from one generator 420 with a summing circuit device 440 to apply a substantially constant DC bias, or offset, to the electric field 461. In various embodiments, the output from the DC supply 430 can be applied directly to one of the electrodes 415 or 425. This DC bias can be used, e.g., to place a selected species of ions in a "balanced" condition between the electrodes, so they will pass through the electrodes with substantially no drift in the y direction. In various embodiments, the voltage from the DC supply is controllably alterable between about 0 volts and about 500 volts. The two high-voltage waveform drivers 410 and 420 and the DC supply 430 share a common ground 390. The circuit elements and electrodes can be connected with electrical cables 450 suitable for carrying high-speed signals. In various embodiments, some of the cables are 50-ohm BNC cables rated for high-voltage operation.

FIG. 4B depicts a various embodiments incorporating high-voltage waveform stabilization. For example, the waveform from one driver 410 is sensed and fed back to the other driver 421. In various embodiments, internal or external circuitry monitors the amplitude and phase of at least one waveform driver 410 and controllably alters the amplitude and phase of the compliment driver 421 so as to maintain a substantially constant relative phase difference $\phi r$ between the two waveforms, and/or maintain a substantially constant peak amplitude ratio $V_{a(pk)}/V_{b(pk)}$ for the two waveforms.

Figure 5A:
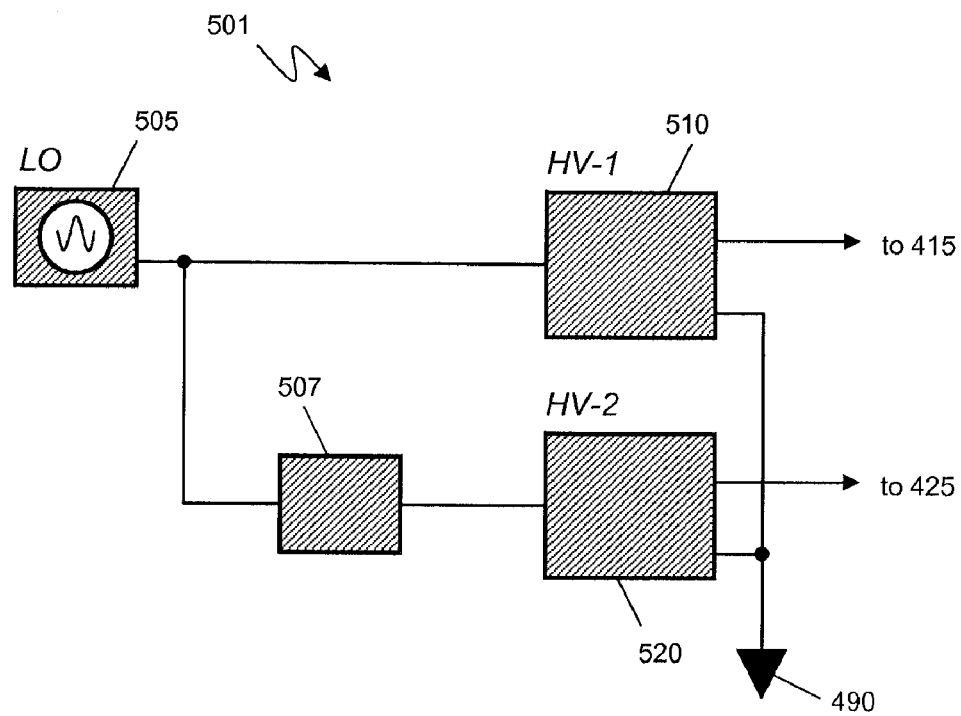
FIGS. 5A-5D represent block diagrams of embodiments of electronic circuits providing high-voltage signals for exciting electrodes of the apparatus depicted in FIGS. 4A-4B.

In various embodiments, circuit components for the high-field asymmetric-waveform apparatus are shown in FIGS. 5A-5D. Referring to FIG. 5A, a local oscillator 505 can be used to create a sinusoidal signal. Part of the output from the oscillator can be amplified by a first high-voltage driver 510 and applied to one electrode 415. Part of the output from the local oscillator can be fed through a frequency converter 507 before amplification by a second high-voltage driver 520 and application to the second electrode 425, and facilitates defining and maintaining the frequency relationship between the two drivers. The drivers 510 and 520 can share a common ground 490. The frequency converter 507 can be used to double, halve, etc., the frequency from the local oscillator 505. For example, the converter 507 can comprise an AC-coupled, filtered, full-wave rectifier which can provide a doubled frequency. For example, the converter 507 can comprise a divide-by-n circuit component, where n=2, or it can comprise a low-pass filter with a cut-off frequency of about one-half the value of the local oscillator frequency. In various embodiments, the high-voltage drivers 510 and 520 can each have internal circuitry to permit adjustments to the output waveform's amplitude and phase.

Figure 5B:
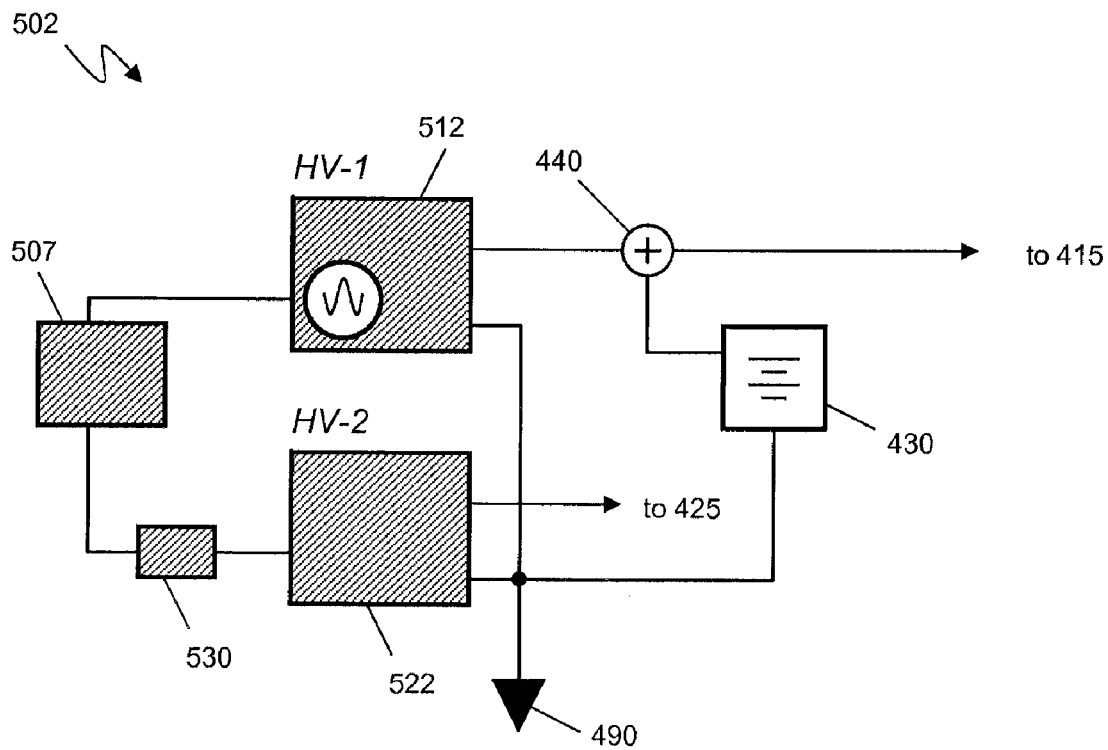
Figure 5C:
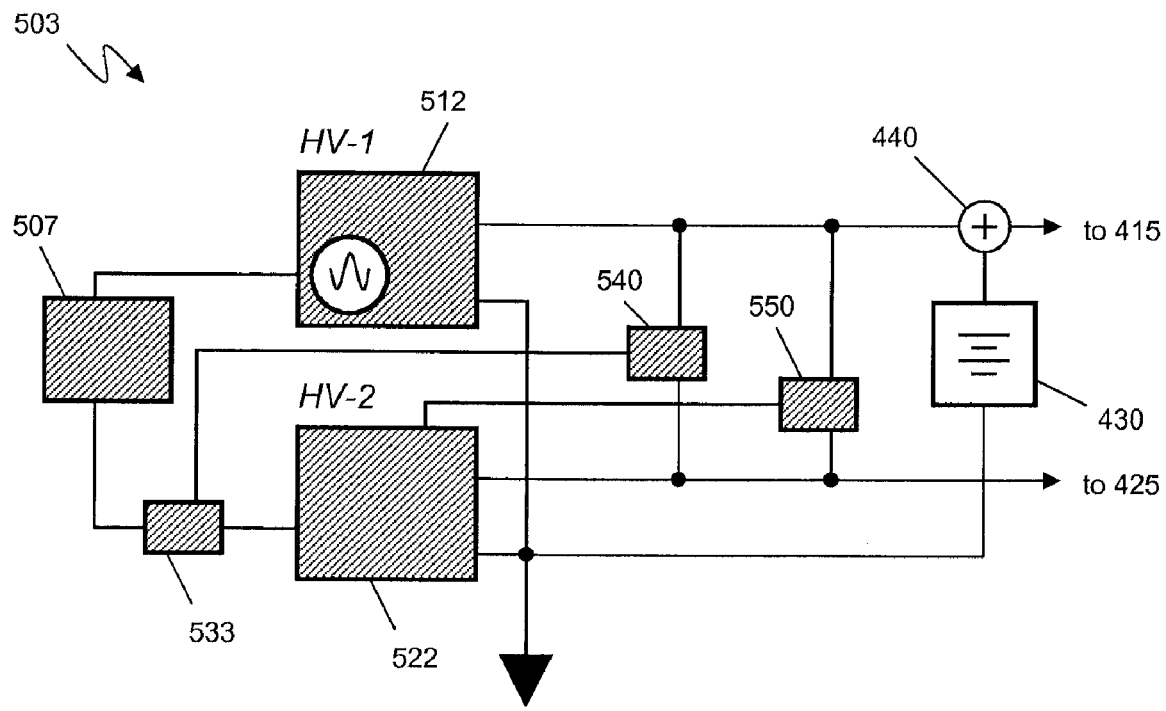

FIGS. 5B-5C depict various embodiments of the high-field asymmetric-waveform apparatus where one high-voltage driver 512 includes an internal local oscillator. Part of the output waveform from the oscillator can be fed through a frequency converter 507, through an external phase-adjusting device 530, 533, and to the second driver 522. The external phase-adjusting component can be used to set a relative phase difference between the two high-voltage waveforms, applied to 415 and 425, within a range between about 0 radians to about $2\pi$ radians. A high-voltage summing circuit 440 and DC power supply 430 can be used to provide an offset, or DC bias, to the electric field appearing between the electrodes 415 and 425.

In various embodiments, waveform stabilization circuitry is incorporated into the high-field asymmetric-waveform apparatus as schematically depicted in FIG. 5C. In various embodiments, phase-detection circuit device 540 senses and compares the phases of each output high-voltage waveform applied to electrodes 415 and 425, and feeds back a signal to the phase-adjusting device 533 so as to maintain a substantially constant relative phase difference $\phi r$ between the two high-voltage waveforms. In various embodiments, amplitude detection circuit device 550 senses and compares the peak amplitudes of each high-voltage waveform, and feeds back a signal to at least one high-voltage driver 522 to maintain a substantially constant peak amplitude ratio $V_{a(pk)}/V_{b(pk)}$ between the two high-voltage waveforms. In various embodiments, phase and amplitude detection and comparison can be carried out within one device.

Figure 5D:
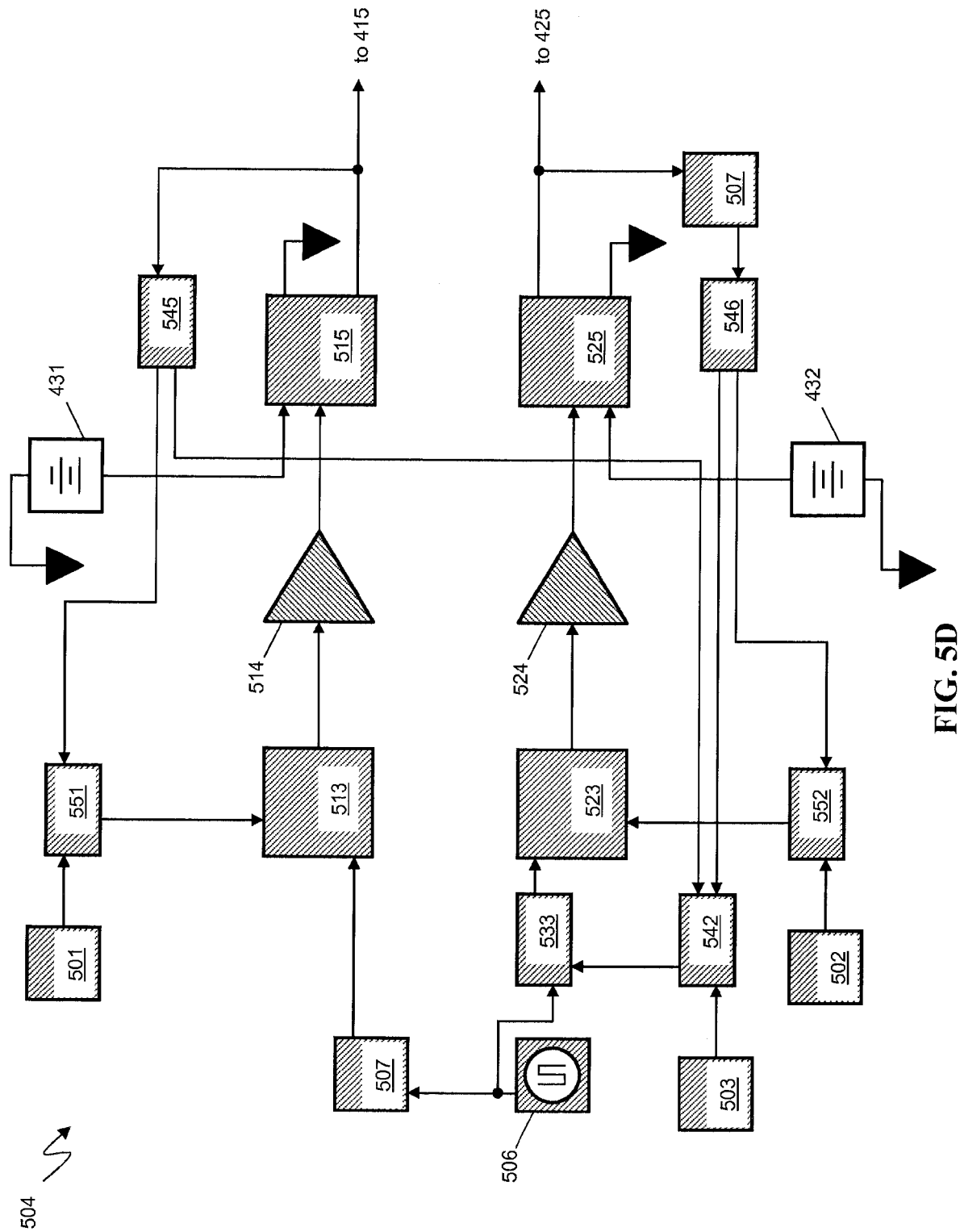

FIG. 5D depicts various embodiments of the high-field asymmetric-waveform apparatus which incorporate a clock source 506, pulse-width modulators 513, 523, power amplifiers 514, 524 and tank circuits 515, 525 to produce high-voltage waveforms for each electrode. In various embodiments, amplitude reference values are set by stable voltage sources 501, 502 which respectively provide reference signals for peak-amplitude comparators 551, 552. The other input to the peak-amplitude comparators can be derived from phase-and-peak-amplitude sensors 545, 546 which sample the high-voltage waveforms applied to the electrodes 415 and 425. Output from the peak-amplitude comparators are fed to pulse width modulators 513 and 523, and can be used to maintain the voltage waveform amplitudes from the modulators at a substantially constant pre-desired value. The peak amplitude ratio between the voltage waveforms can be set by adjusting the stable voltage sources 501, 502.

The oscillation frequency for each pulse-width modulator 513, 523 can be derived from a single clock source 506. In various embodiments, the frequency output from the clock source is divided by two at the frequency converter 507 before providing a reference clock signal for pulse-width modulator 513. In various embodiments, the frequency output from the clock source 506 is fed into a phase-adjusting device 533 before providing a reference clock signal for pulse-width modulator 523.

In various embodiments, outputs from the pulse-width modulators 513, 523 are fed into power amplifiers 514, 524 which drive two separate tank circuits 515, 525. The tank circuits can comprise inductive and capacitive elements which store electrical energy and reduce overall power requirements for driving electrodes 415 and 425. The inductive and capacitive values in the tank circuits can be chosen such that their resonant frequency characteristic is substantially equal to the drive frequency established at each pulse-width modulator. In various embodiments, two DC power supplies 431, 432 can be used to provide offsets or bias to the high-voltage waveforms from each tank circuit.

In various embodiments, the high-voltage output from each tank circuit 515, 525 is sampled with peak-amplitudeand-phase sensing circuit devices 545, 546, respectively. The sensed amplitude values are fed back to the amplitude comparitors 551, 552 to maintain a substantially constant peak-amplitude ratio $V_{a(pk)}/V_{b(pk)}$. The phase of the low-frequency waveform, e.g. that detected at device 545, can be fed directly back to a phase comparator 542. For the high-frequency waveform, a sampled signal may be frequency halved by a second converter 507 prior to phase detection. The detected phase may then be fed back to phase comparator 542. A relative phase difference reference value from phase-reference source 503 may also be applied to comparator 542. Output from the phase comparator can be applied to the phase-adjusting device 533 so as to maintain a substantially constant relative phase difference between the two high-voltage signals applied to the electrodes 415, 425. In various embodiments, two phase comparators can be used instead of one. For example, a first phase comparator can compare phases detected from the two devices 545, 546, and its output fed to a second comparator. The second phase comparator can receive as its second input the output from the phase-reference source 503, and can feed its output to the phase adjusting device 533.

While the present teachings have been described in conjunction with various embodiments and examples, it is not intended that the present teachings be limited to such embodiments or examples. For example, although the embodiments are directed to driving electrodes for FAIMS instruments, equivalent apparatus may be useful for driving electrodes in electro-optical instruments. While the present teachings illustrated have been illustrated in terms of a planar differential mobility devise, it will be apparent to those skilled in the art that these principles apply to cylindrical and other curved geometries. On the contrary, the present teachings encompass various alternatives, modifications, and equivalents, as will be appreciated by those of skill in the art.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

The claims should not be read as limited to the described order or elements unless stated to that effect. It should be understood that various changes in form and detail may be made by one of ordinary skill in the art without departing from the spirit and scope of the appended claims. All embodiments that come within the spirit and scope of the following claims and equivalents thereto are claimed.

What is claimed is:

1. A high-field asymmetric-waveform apparatus for a differential ion mobility spectrometer comprising:
   a first electrode;
   a second electrode with substantially constant spacing to the first electrode;
   a first high-voltage waveform generator producing a sinusoidal waveform at a first frequency and at a first amplitude, the first waveform generator electrically connected to the first electrode, the first frequency value being adjustable and first amplitude value being adjustable;
   a second high-voltage waveform generator, electrically producing a sinusoidal waveform at a second frequency and at a second amplitude, the second waveform generator electrically connected to the second electrode, the second frequency value being adjustable and second amplitude value being adjustable, the second frequency value being a harmonic of the first frequency value;
   a phase adjusting circuit adapted to adjust the phase of at least one of the waveform generators; wherein
   the electric field created between the first electrode and second electrode, resulting from the application of the first high-voltage waveform and second high-voltage waveform, is asymmetric and has a time-averaged value substantially equal to zero.

2. The apparatus as claimed in claim 1 further comprising an adjustable direct-current voltage source electrically connected to at least one of the first or second electrodes.

3. The apparatus as claimed in claim 1 wherein the first electrode and the second electrode are substantially planar electrodes.

4. The apparatus as claimed in claim 1 wherein the magnitude of the field created between the first electrode and second electrode for at least a portion of the waveform cycle is greater than about 5,000 volts $cm^{-1}$.

5. The apparatus as claimed in claim 1 wherein the first frequency is greater than about 600 KHz.

6. The apparatus as claimed in claim 1 wherein the second frequency is obtained from electronically doubling the first frequency.

7. The apparatus as claimed in claim 1 wherein the first frequency is obtained by electronically dividing the second frequency.

8. The apparatus as claimed in claim 1 wherein the first frequency is obtained by electronically filtering the second frequency.

9. The apparatus as claimed in claim 1 further comprising an amplitude-controlling circuit coupled to the first waveform generator and second waveform generator, the amplitude-controlling circuit maintaining the ratio of the first amplitude to the second amplitude at a substantially constant value.

10. The apparatus as claimed in claim 1 further comprising a phase-controlling circuit coupled to the first waveform generator and second waveform generator, the phase-controlling circuit maintaining the relative phase difference between the first waveform and second waveform at a substantially constant value.

11. The apparatus as claimed in claim 1 where the two electrodes are planar in geometry.

12. The apparatus as claimed in claim 1 where the two electrodes are formed in a curved geometry.

13. The apparatus as claimed in claim 1 where first high-voltage waveform generator and the second high-voltage waveform generator comprise a single high-voltage generator.

14. A method of providing an asymmetric electric field for differential ion mobility spectrometry comprising:
   providing a first electrode with substantially constant spacing to a second electrode;
   applying to the first electrode a first high-voltage substantially sinusoidal waveform at a first frequency and at a first amplitude;
   applying to the second electrode a second high-voltage substantially sinusoidal waveform at a second frequency and at a second amplitude;
   selecting the second frequency to be substantially a harmonic of the first frequency value; and
   selecting a ratio of the first amplitude to the second amplitude and a relative phase difference between the first waveform and the second waveform to provide an electric field between the first electrode and the second electrode which is asymmetric and has a time-averaged value substantially equal to zero.

15. A method according to claim 14 further comprising applying a direct-current voltage to at least one of the first or second electrodes.

16. A method according to claim 14 wherein the magnitude of the field created between the first electrode and the second electrode for at least a portion of the waveform cycle is greater than about 5,000 volts $cm^{-1}$.

17. A method according to claim 14 wherein the first frequency is greater than about 600 KHz.

18. A method according to claim 14 further comprising electronically doubling the first frequency to obtain the second frequency.

19. A method according to claim 14 further comprising electronically dividing the second frequency to obtain the first frequency.

20. A method according to claim 14 further comprising electronically filtering the second frequency to obtain the first frequency.

21. A method according to claim 14 further comprising using a sensing and feedback circuit to electronically maintain the ratio of the first amplitude to the second amplitude at a substantially constant value.

22. A method according to claim 14 further comprising using a sensing and feedback circuit to electronically maintain the relative phase difference between the first waveform and second waveform at a substantially constant value.

* * * * *